US00PP31355P2

(12) United States Plant Patent
Hansen

(10) Patent No.: US PP31,355 P2
(45) Date of Patent: Jan. 14, 2020

(54) ***ACHILLEA* PLANT NAMED 'SASSY SUMMER SANGRIA'**

(50) Latin Name: ***Achillea sibirica* (synonym)**
Varietal Denomination: Sassy Summer Sangria

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,529

(22) Filed: Nov. 28, 2018

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
See application file for complete search history.

*Primary Examiner* — Anne Marie Grunberg

(57) ABSTRACT

The new and distinct Yarrow, *Achillea* plant named 'Sassy Summer Sangria', with narrow, silvery, fern-like foliage; tall, stiff, heavily branched peduncles with dark red inflorescences, beginning in late spring and continuing for about six weeks. The new plant is useful for landscaping, as a specimen or en masse and as a cut flower.

1 Drawing Sheet

Botanical designation: *Achillea sibirica* (synonym).
Cultivar denomination: 'Sassy Summer Sangria'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 9, 2018. Prior to that, on Nov. 28, 2017 the claimed plant was displayed as a photograph without description in a calendar distributed to customers of Walters Gardens, Inc., who obtained the plant and all information relating thereto, from the inventor. No plants of *Achillea* 'Sassy Summer Sangria' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct yarrow herein also referred to as *Achillea* 'Sassy Summer Sangria', by the cultivar name, 'Sassy Summer Sangria', or as the new plant. The new plant was selected by the inventor as a single seedling resulting from a cross in an isolation block between a proprietary unreleased plant identified with the breeder code 13-5-14 (not patented) crossed with siblings of 13-5-14 in research facility of a wholesale perennial grower based in Zeeland, Mich., USA. The seeds from this cross were collected on Sep. 23, 2014. The single seedling was then isolated and compared in subsequent years to other Yarrow and subsequently found to be different from all cultivars known to the discoverer and eventually given the breeder code 14-29-2.

Asexual propagation at the same nursery in Zeeland, Mich., USA by cuttings has shown 'Sassy Summer Sangria' to be stable and reproduce true to type in successive generations.

SUMMARY OF THE PLANT

*Achillea* 'Sassy Summer Sangria' has not been observed in all possible environmental conditions. The phenotype may vary slightly with changes in environments such as light intensity, fertility, water availability, etc. without, however any variation in genotype.

*Achillea* 'Sassy Summer Sangria' is distinct from all cultivars known to the inventor in the following traits:

1. Narrow, silvery, fern-like foliage with tall height and dense upright habit.
2. Numerous large panicles of dark red inflorescences.
3. Heavily-branched peduncles with center main cluster to about 18 cm across.
4. Sturdy stems withstand wind and rain.
5. Long flowering period beginning late spring and continuing for about six weeks.

Plants of *Achillea* 'Sassy Summer Sangria' are most similar to 'Red Velvet' (not patented) 'Strawberry Seduction' U.S. Plant Pat. No. 18,401 and 'Red Beauty' (not patented). 'Red Velvet' has thinner more flexible stems and the foliage is not as silvery. 'Red Beauty' is shorter in habit, has less stiff stems and the flowers are slightly more pinkish. 'Strawberry Seduction' has more lax flower stems, the foliage is less silvery-glaucous and not as thick in substance, the flower stems have less branching and the flowers are a different color. 'Sunny Seduction' U.S. Plant Pat. No. 20,808 has inflorescences with bright yellow-colored florets, the foliage is smaller, and foliage color is less silvery-glaucous.

BRIEF DESCRIPTION OF THE DRAWINGS

The color drawings illustrate the overall characteristics of *Achillea* 'Sassy Summer Sangria' as a three-year-old plant. The colors are as true as reasonably possible given the technology available. The color values may vary slightly depending on light intensity and quality.

DETAILED BOTANICAL DESCRIPTION

Figure 1:
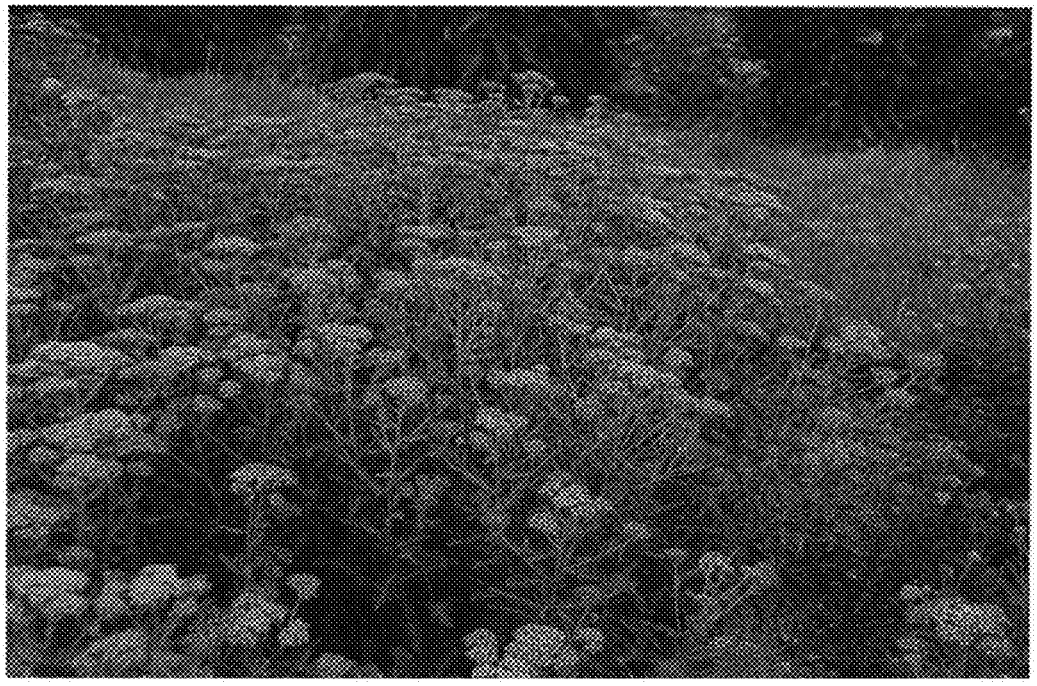
FIG. 1 shows the new plant in a trial facility.
Figure 2:
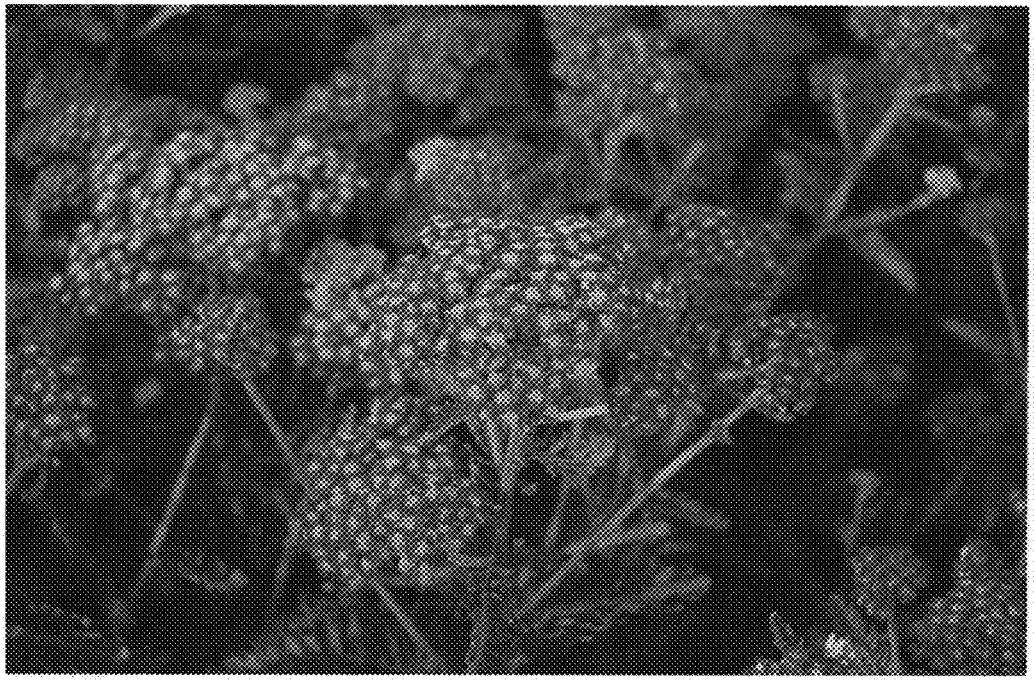
FIG. 2 shows a close-up of the flowers of the new plant.

The following description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent 13-5-14 is either *Achillea millefolium* 'Strawberry Seduction' U.S. Plant Pat. No. 18,401 x *sibirica* or *Achillea millefolium* 'Sunny Seduction' U.S. Plant Pat. No. 20,808 x *sibirica*; male or pollen parent unknown;

Asexual propagation: Shoot tip cuttings, about 10 to 14 days to initiate roots; time to finish as #1 field grown size about 9 months;

Plant habit: Dense axillary branches; upright, heavily-branched, herbaceous, winter-hardy, perennial mound; up to 72.0 cm wide and 70.0 cm tall; average about 65.0 cm across and about 65.0 cm tall;

Leaves: Alternate; glabrous; pinnatisect; lanceolate; acute apex; base attenuate; sessile except most proximal leaves; lanulose abaxial and adaxial; up to 31.0 cm long and 5.5 cm wide with individual lobes to 14.0 mm wide and 3.2 cm long, average about 14.2 cm long and 4.0 cm wide;

Leaf color: Young expanding leaves adaxial blend between RHS 189B and RHS N138D and abaxial blend between RHS 189B and RHS N138C; mature leaves adaxial nearest RHS N138B, abaxial nearest RHS N138C;

Veins: Pinnate; only abaxial midrib obvious;

Midrib color: Adaxial nearest RHS 193D and abaxial nearest RHS 192C;

Inflorescence: Radiate; composite consisting of about five ray and about twelve disk florets; on heavily branched terminal stems; individual inflorescence about 4.5 mm diameter, about 4.5 mm tall from bottom of involucral bracts to top of exserted stigmas; disk about 2.0 mm across; attitude mostly upright; producing branched stems with about 400 inflorescences per stem;

Receptacle: About 3.0 mm tall; color nearest RHS 148C;

Inflorescence fragrance: Not detected;

Phyllaries: About ten in two whorls; lanceolate; acute apex; truncate base; margin entire; outer or lower set about 2.0 mm long and 1.0 mm across, inner set about 3.0 mm long and 1.0 mm across; glabrous adaxial, pubescent abaxial; tight adpressed against ray petals;

Phyllary color: In low light exposure lower set nearest RHS 147C adaxial and abaxial, upper set nearest RHS 147B adaxial and abaxial; in high light exposure abaxial develops to nearest RHS 177A in center and nearest RHS NN155B along margins;

Flowering period: Mid-June, for about 6 weeks;

Flower longevity: 4 to 6 days;

Inflorescence buds: With ray florets still erect 5.0 mm tall and 2.0 mm across; ovoid;

Inflorescence bud color: Ray florets while still upright exposed petal color nearest RHS 53A distally and nearest RHS NN155C just above phyllaries; phyllaries color variable between RHS 177A and RHS 147C;

Peduncle: Cylindrical; lanulose; strong; upright attitude; heavily branched; up to 7.0 mm diameter at base, average 5.0 mm diameter; and 65.0 cm long, flowering in upper 20.0 cm; branches to about 15.0 cm long and 4.0 mm diameter at base;

Peduncle color: Between RHS 189A and RHS 189B;

Ray florets: Imperfect; staminate; typically about five per inflorescence; containing only gynoecium with style about 2.5 mm long and split stigma;

Ray floret ligule: Rounded with basal claw; apex rounded to slightly emarginate, margin entire; base claw, attenuate; opening flat to form 180° angle; glabrous adaxial and adaxial; about 4.0 mm long and about 5.0 mm wide; basal claw about 1.5 mm long and about 0.5 mm across;

*Young ray floret ligule color when first flat.*—Adaxial between RHS 46A and RHS 53A, abaxial nearest RHS 65D and base nearest RHS NN155C.

*Mature ray floret ligule color.*—Adaxial nearest RHS 65D with center portion between RHS 53B and RHS 53C; abaxial lighter than RHS 65D.

*Style.*—Cylindrical; about 2.0 mm long and 0.2 mm diameter; exserted; color nearest RHS 18B.

*Stigma.*—Bifid; about 1.5 mm long and 0.2 mm diameter; color nearest RHS 18B.

Disk Florets: About twelve per capitulum; tubular; glabrous; consisting of tepals, staminal tube and pistil; size about 3.5 mm long by 1.0 mm wide at apex;

*Tepals.*—Five; 2.5 mm long and 0.7 mm wide, fused in the basal 2.0 mm, acute apex.

*Tepal color.*—Nearest RHS 31B.

*Staminal tube.*—Made up of five adnate stamens; about 2.0 mm long.

*Filaments.*—Cylindrical; about 0.7 mm long and 0.1 mm diameter; color nearest RHS NN155A.

*Anther.*—About 1.0 mm long; color nearest RHS 13B.

*Pollen.*—Fine, round, closest to RHS 13A.

*Style.*—Bifid; cylindrical; exserted; about 2.0 mm long and 0.2 mm diameter; color nearest RHS 18B.

*Stigma.*—Bifid; reflexing as it matures; about 1.5 mm long; color nearest RHS 18B.

Seed: Flattened deltoid; acute apex and truncate base; surface glabrous; about 2.0 mm long and 0.7 mm across base;

Seed color: Between RHS 165A and RHS 165B in center and RHS 161D around edges; *Achillea* 'Sassy Summer Sangria' is tolerant of winter temperatures as low as −35° C. and summer temperatures as high as 38° C. It is not known to be tolerant of diseases and pest that are common to other *Achillea* cultivars.

I claim:

1. The new and distinct cultivar of *Achillea* plant named 'Sassy Summer Sangria' as described and illustrated.

* * * * *